United States Patent [19]
Lowy et al.

[11] Patent Number: 5,855,891
[45] Date of Patent: Jan. 5, 1999

[54] ICHIMERIC PAPILLOMAVIRUS-LIKE PARTICLES

[75] Inventors: Douglas R. Lowy, Bethesda; John T. Schiller; Heather Greenstone, both of Silver Spring, all of Md.

[73] Assignee: The United States of America as represented by the Department of Health and Human Services, Washington, D.C.

[21] Appl. No.: 781,084

[22] Filed: Jan. 9, 1997

Related U.S. Application Data

[60] Division of Ser. No. 319,467, Oct. 6, 1994, Pat. No. 5,618, 536, which is a continuation-in-part of Ser. No. 32,869, Mar. 16, 1993, Pat. No. 5,437,951, which is a continuation-in-part of Ser. No. 941,371, Apr. 3, 1992.

[51] Int. Cl.$^6$ .......................... A61K 39/00; A61K 39/12; C12P 21/06; C12N 7/00
[52] U.S. Cl. ................................. 424/192.1; 424/204.1; 435/69.1; 435/235.1; 435/236
[58] Field of Search .............................. 435/235.1, 240.2, 435/69.1, 254.2, 320.1, 236, 317.1; 530/412, 413; 424/192.1, 204.1

[56] References Cited

FOREIGN PATENT DOCUMENTS

| | | |
|---|---|---|
| WO9300436 | 1/1993 | WIPO . |
| WO9302184 | 2/1993 | WIPO . |
| WO9405792 | 3/1994 | WIPO . |

OTHER PUBLICATIONS

Alloub et al., (1989) Human papillomavirus infection and cervical intraepithelial neoplasia in women with renal allografts. Br. Med. Journal 298:153–156.
Baker et al. (1991) Structures of bovine and human papillomaviruses. Biophys J. 60:1445–1456.
Borisova et al. (1989) Recombinant core particles of hepatitis B virus exposing foreign antigenic determinants on their surface. FEBS Letter 259:121–124.
Brown et al. (1994) Chimeric parvovirus B19 capsids for the presentation of foreign epitopes. Virology 198:477–488.
Chen et al. (1991) Human papillomavirus type 16 nucleoprotein E7 is a tumor rejection antigen. Proc. Natl. Acad. Sci. 88:110–114.
Christensen, N.D. and Kreider, J. (1990) Antibody–Mediated neutralization in vivo of infectious papillomaviruses. Journal of Virology 64(7):3151–3156.
Christensen, N.D. and Kreider, J. (1993) Monoclonal antibody neutralization of BPV–1. Virus Research 28:195–202.
Christensen, N.D. et al. (1990) Monoclonal antibody–mediated neutralization of infectious human papillomavirus type 11. Journal of Virology 64:5678–5681.
Christensen, N.D. et al. (1991) The open reading frame L2 of cottontail rabbit papillomaviurs contains antibody–inducing neutralizing epitopes. Virology 181:572–579.
Crawford, L. (1993) Prospects for cervical cancer vaccines. In Cancer Surveys 16:215–229.

Dvoretzky et al. (1980) A quantitative in vitro focus assay for bovine papilloma virus. Virology 103:369–375.
Feltkemp et al. (1993) Vaccination with cytotoxic T lymphocyte epitope–containing peptide protects against a tumor induced by human papillomavirus type 16–transformed cells. Eur. J. Immunol. 23:2242–2249.
Francis et al. (1990) Immunological properties of hepatitis B core antigen fusion proteins. Proc. Natl. Acad. Sci. 87:2545–2549.
Griffiths et al. (1991) Induction of high–titer neutralizing antibodies using hybrid human immunodeficiency virus V3–Ty viruslike particles in a clinically relevant adjuvant. J. Virol. 65:450–456.
Hagensee et al. (1993) Self–assembly of human papillomavirus type 1 capsids by expression of the L1 protein alone or by coexpression of the L1 and L2 capsid proteins. J. Virol. 67:315–322.
Hartig, P.C. (1991) Generation of recombinant baculovirus via liposome–mediated transfection. Biotechniques 11:310–312.
Higuchi, R. (1990) Recombinant PCR. PCR Protocols; A guide to methods and applications p. 177.
Howley, P.M. (1990) Papillomavirinae and their replication. In Virology, 2d Edition (Fields, B.N. & Knipe, D.M.; eds.) p. 1627.
Kirnbauer et al. (1994) A virus–like particle enzyme–linked immunosorbent assay detects serum antibodies in a majority of women infected with human papillomavirus type16. Journal of the National Cancer Institute 86:494–499.
Kirnbauer et al. (1993) Efficient self–assembly of human papillomavirus type L1 and 16 L1–L2 into virus–like particles. Journal of Virology 67:6929–6936.
Kirnbauer et al. (1992) Papillomavirus L1 major capsid protein self–assembles into virus–like particles that are highly immunogenic. Proc. Natl. Acad. Sci. 89:12180–12184.
Laga et al. (1992) Genital papillomavirus infection and cervical dysplasia–opportunistic complications of HIV infection. Int. J. Cancer 50:45–48.
Michel et al. (1990) T– and B–lymphocyte responses to human immunodeficiency virus (HIV) type 1 in macaques immunized with hybrid HIV/hepatitis B surface antigen particles. J. Viro. 64:2452–2455.
Miyamura et al. (1994) Parvovirus particles as platforms for protein presentation. Proc. Natl. Acad. Sci. USA 91:8507–8511.

(List continued on next page.)

*Primary Examiner*—Ponnathapura Achutamurthy
*Assistant Examiner*—Hankyel T. Park
*Attorney, Agent, or Firm*—Knobbe, Martens, Olson & Bear, LLP

[57] ABSTRACT

The present invention provides a papillomavirus-like particle having conformational epitopes comprising a papillomavirus L1 fusion product and, optionally, a papillomavirus L2 product; and related DNA molecules, host cells, and methods.

10 Claims, No Drawings

OTHER PUBLICATIONS

Mose Larson et al. (1987) Proteins present in bovine papillomavirus particles. J. Virol. 61:3596–3601.

Pilacinski et al. (1984) Cloning and expression in *escherichia coli* of the bovine papillomavirus L1 and L2 open reading frames. Bio/technology 2:356–360.

Roden et al. (1994) Interaction of papillomavirus with the cell surface. J. Virol. (in press).

Rose et al. (1993) Expression of human papillomavirus type 11 L1 protein in insect cells: in vivo and in vitro assembly of viruslike particles. J. Virol. 67:1936–1944.

Schiffman, M.H. (1992) Recent progress in defining the epidemiology of human papillomavirus infection and cervical neoplasia. J. Natl. Cancer Inst. 84:394–398.

Segre et al. (1955) Neutralization of bovine papilloma virus with serums from cattle and horses with experimental papillomas. Am. J. Vet. Res. 16:517–520.

Summers, M.D. & Smith, G.E. (1987) A manual of methods for baculovirus vectors and insect cell culture procedures, Texas Agricultural Experiment Station Bulletin vol. 1555.

Tindle et al. (1994) Chimeric hepatitis B core antigen particles containing B– and Th–epitopes of human papillomavirus type 16 E7 protein induce specific antibody and T–helper responses in immunised mice. Virology 200:547–557.

Viscidi et al. (1993) Serologic response in human papillomavirus–associated invasive cervical cancer. Int. J. Cancer 55:780–784.

Zur Hausen, H. (1991) Viruses in human cancers. Science 254:1167–1173.

Kirnbauer, R. et al. (1994) A vaccine of virus–like particles made in insect cells can inhibit papillomavirus infection of rabbits. 13th International Papillomavirus Conference, Amsterdam, The Netherlands.

ICHIMERIC PAPILLOMAVIRUS-LIKE PARTICLES

CROSS-REFERENCE TO RELATED APPLICATIONS

This application is a division of U.S. patent application Ser. No. 08/319,467, filed Oct. 6, 1994, U.S. Pat. No. 5,618,536, which was a continuation-in-part of U.S. patent application Ser. No. 08/032,869, filed Mar. 16, 1993, now U.S. Pat. No. 5,437,951, which was a continuation-in-part of U.S. patent application Ser. No. 07/941,371, filed Sep. 3, 1992. These applications and all patent applications, patents and publications cited hereunder are incorporated herein by reference.

FIELD OF THE INVENTION

The present invention relates to chimeric papillomavirus-like particles and related synthetic DNA molecules, host cells, methods and vaccines.

BACKGROUND OF THE INVENTION

Papillomaviruses infect the epithelia of humans and a wide variety of animals, where they generally induce benign proliferation at the site of infection. However, in some cases the lesions induced by certain papillomaviruses undergo malignant progression. There is a strong association between malignant progression of human genital lesions and certain human papillomavirus (HPV) types, such as HPV16. Infection by one of these types is considered the most significant risk factor in the development of cervical cancer, one of the most common cancers of women worldwide (zur Hausen, H., Science 254:1167 (1991); Schiffman, M. H., J. Natl. Cancer Inst. 84:394 (1992)). The majority of cervical carcinomas contain and express HPV early genes, such as E6 and E7, and these genes have been shown to have potent transforming and immortalizing activity in cultured cells (Werness, B. A., Munger, K. & Howley, P. M. (1991) Advances in Oncology, eds. DeVita V. T., Hellman, S. & Rosenberg, S. A. (Lipponcott, Philadelphia) pp. 3–18).

Papillomaviruses are non-enveloped double-stranded DNA viruses about 55 nm in diameter with an approximately 8 kb genome in the nucleohistone core (Baker, et al., Biophys J 60:1445 (1991)). The capsids are composed of two virally-encoded proteins, L1 and L2, that migrate on SDS-PAGE gels at approximately 55 kDa and 75 kDa, respectively (Mose Larson et al., J. Virol. 61:3596 (1987)). L1, which is the major capsid protein, is arranged in 72 pentameters which associate with T=7 icosahedral symmetry. The function and position within the virion of L2 are unclear (Baker, et al., Biophys J 60:1445 (1991)).

The L1 protein has the capacity to self-assemble so that large amounts of virus-like particles (VLPs) may be generated by expression of the L1 protein from a number of species of papillomavirus in a variety of recombinant expression systems (Hagensee et al., J Virol 67:315 (1993); Kirnbauer et al., Proc Natl Acad Sci USA 89:12180 (1992); Kirnbauer et al., J Virol 67:6929 (1993); Rose et al., J Virol 67:1936 (1993)). Although not required for assembly, L2 is incorporated into VLPs when co-expressed with L1 (L1/L2 VLPs) in cells.

Immunization of rabbits with native virions or L1 VLPs, but not with non-assembled L1 expressed in E. coli, induces high titers of neutralizing serum antibodies (Christensen, N. D. and Kreider, J. W., J Virol 64:3151 (1990); Kirnbauer et al., Proc Natl Acad Sci USA 89:12180 (1992); Pilacinski et al., Bio/Technology 2:356 (1984); Segre et al., Am. J. Vet. Res. 16:517 (1955)). The polyclonal and monoclonal antibodies generated against native particles recognize conformationally dependent epitopes (Christensen, N. D. and Kreider, J. W., Virus Res 28:195 (1993); Christensen et al., J Virol 64:5678 (1990); Christensen et al., Virology 181:572 (1991)).

Neutralizing antibodies generated against VLPs also recognize conformationally dependent epitopes. Using infectious BPV1, which can be readily obtained from bovine lesions, and a quantitative in vitro BPV1 infectivity assay (Dvoretzky et al., Virology 103:369 (1980)), workers showed VLPs from bovine papillomavirus induced high levels of neutralizing antibodies (Kirnbauer et al., Proc Natl Acad Sci USA 89:12180 (1992)). The neutralizing antibodies were directed against conformationally dependent epitopes, in that denaturation of the particles prior to immunization abolished the ability of the preparation to induce neutralizing activity (id.).

When the L1 gene of a HPV16 isolate derived from a nonprogressed lesion was used to express the L1 major capsid protein in insect cells via recombinant baculoviruses, L1 self-assembled into VLPs at a yield 3 orders of magnitude higher than what had been obtained using L1 derived from the prototype HPV16 (originally isolated from a cancerous lesion), and formed VLPs that were morphologically similar to native virions (Kirnbauer et al., J Virol 67:6929 (1993)). DNA sequence comparison identified a single non-conserved amino acid change to be responsible for the inefficient self-assembly of the prototype L1 (id.). The L1 of the assembly-competent clone is thus considered to be the wild-type gene, and the prototype L1 of the assembly-defective clone a mutant.

Using HPV16 VLPs of the wild-type L1 protein as antigens, an ELISA was developed that detected serum antibodies in patients infected with HPV16 (Kirnbauer et al., J. Natl. Cancer Inst. 86:494 (1994)). In contrast, neither denatured HPV16 particles nor preparations of the prototype L1 protein could detect these antibodies (id.). These results demonstrate that the prototype L1 protein does not present conformational epitopes.

Rabbit serum raised against self-assembled wild-type HPV16 L1/L2 virus-like particles was discovered to prevent HPV16 VLP binding to cell surface molecules (Roden et al., J. Virol., in press, (November, 1994)). In contrast, serum raised against the prototype strain of HPV16 L1/L2 did not prevent such binding (id.). The data show that the prototype HPV16 strain lacks conformational epitopes.

Rabbits immunized with intact cottontail rabbit papillomavirus (CRPV) virus-like particles composed of L1 or L1/L2 were protected from subsequent experimental challenge by infectious CRPV (Breitburd et al., 12th International Papillomavirus Workshop in Amsterdam, in press, (October 1994)). In contrast, those immunized with denatured particles were not protected (id.). These findings are consistent with the conclusion that VLPs presenting conformational epitopes are able to induce protective immunity.

VLPs composed of capsid proteins are attractive candidates for prophylactic vaccines to prevent papillomavirus infection. However, it is unlikely that these VLP vaccines would have therapeutic effects against established papillomavirus infections. The capsid proteins, unlike E6 and E7, are not detectably expressed in progressed lesions or in infected basal epithelial cells, which are the presumed targets in immune regression of papillomas.

There is evidence from experimental models that immunity against papillomavirus proteins other than L1 and L2 might help control papillomavirus infection. Since E6 and E7 are selectively maintained during oncogenic progression, there is the possibility that peptides derived from these oncoproteins could serve as targets for cell-mediated immune responses to HPV-containing tumor cells. Studies in animal models suggest the E7 protein of HPV16 acts as a tumor rejection antigen (Chen et al., Proc. Natl. Acad. Sci. USA 88:110 (1991); Feltkemp et al., Eur. J. Immunol. 23:2242 (1993)). Moreover, the frequency of HPV infection, persistence of HPV infection, and risk of developing cervical cancer and other HPV-related cancers is increased in patients with depressed cellular immunity (Allout et al., Br. Med. J. 298:153 (1989); Laga et al., Int. J. Cancer 50:45 (1992)). These observations suggest cell-mediated immunity is important in the defense against HPV infection and its associated tumor development. The induction of such immunity might be therapeutic, as well as prophylactic.

It has been demonstrated that foreign peptides can be incorporated into viral capsid-like structures and these chimeric particles can be used to present foreign antigens to the immune system. Published examples include hepatitis B core antigen particle presentation of human rhinovirus type 2 epitopes (Francis et al., Proc. Natl. Acad. Sci. USA 87:2545 (1990)), gp41 of HIV (Borisova et al., FEBS Lett. 259:121 (1989)), and B19 parvovirus particle presentation of peptides from herpes simplex virus 1 and murine hepatitis virus (Brown et al., Virology 198:477 (1994)). The parvovirus chimeras protected mice from experimental challenge with the corresponding virus. In all of the above systems, foreign sequences have been inserted in proteins integral to the capsid structure and have been limited to less than 20 amino acids. However a recent study (Miyamura et al., Proc. Natl. Acad. Sci. USA 91:8507 (1994)) has demonstrated that the entire 147 aa hen egg white lysozyme protein can be incorporated into B19 parvovirus particles when fused to the parvovirus L1 minor capsid protein. The lysozyme remained biologically active and elicited an immune response when injected into rabbits. In perhaps less relevant studies, hepatitis B virus surface antigen particles (which are lipid membrane structures) containing 84 aa of HIV-1 envelope glycoprotein (Michel et al., J. Virol. 64:2452 (1990)) and yeast Ty virus-like particles containing a portion of HIV-1 V3 loop (Griffiths et al., J. Virol. 65:450 (1991)) have also been shown to produce an immune response to the inserted peptides when inoculated into animals. With respect to papillomaviruses, it was recently reported that hepatitis B core antigen particles containing HPV16 E7 peptides (all less than 20 aa) induced peptide specific antibodies and T-helper responses in mice (Tindle et al., Virology 200:547 (1994)).

Chimeric particles based on self-assembled papillomavirus L1 have not been reported, nor has the use of L2 as a viral fusion partner for purposes of generating chimeric VLPs been described. The chimeric particle studies cited above involve viruses that are unrelated to papillomaviruses and thus cannot predict the results of chimeric particle studies involving papillomaviruses. Indeed, in the papillomavirus study by Kirnbauer et al., J Virol 67:6929 (1993), supra, it was demonstrated that a single nonconserved amino acid change in L1 is responsible for inefficient self-assembly of L1 into VLPs and the presentation of conformational epitopes, which seem to be required for induction and detection of clinically relevant immune reactivity. Thus, the studies using viruses unrelated to papillomavirus cannot predict whether a papillomavirus L2 containing a foreign peptide or protein can co-assemble with papillomavirus L1 into particles, given that a single amino acid substitution in L1 can abolish efficient self-assembly. Neither can these studies predict whether any resulting chimeric particles will retain the ability to induce or detect neutralizing antibodies or other immune related responses, given that a single amino acid substitution in L1 can bar the presentation of conformational epitopes.

It is an object of the present invention to provide chimeric papillomavirus-like particles. These chimeric particles may function as platforms for multivalent antigen presentation. Or they may serve for delivery into cells of proteins for processing into peptides and subsequent presentation of these peptides within the context of MHC molecules to elicit a cell-mediated immune response. The chimeric particles represent a cost effective way to generate an effective papillomavirus vaccine with a broad spectrum of utility. Alternatively, the chimeric papillomavirus-like particles may be applied to VLP and/or fusion partner purification. Or, the particles may operate to deliver into cells intact and active proteins, for example, enzymes, or toxins or drugs.

SUMMARY OF THE INVENTION

According to one aspect of the invention, there is provided a papillomavirus-like particle, characterized as having conformational epitopes, comprising a papillomavirus L1 product and a papillomavirus L2 fusion product.

The papillomavirus L2 fusion product may be characterized as being a human papillomavirus L2 fusion product or a bovine papillomavirus L2 fusion product.

The human papillomavirus L2 fusion product may be characterized as being a HPV16 L2 fusion product and the bovine papillomavirus L2 fusion product may be characterized as being a BPV1 L2 fusion product.

The papillomavirus L2 fusion product may comprise a fusion partner characterized as being a peptide or a full-length protein, or may comprise fusion partners that include peptides or full-length proteins or combinations thereof linked in tandem.

The fusion partner may be a papillomavirus E6 or E7 product.

The papillomavirus L2 fusion product may be characterized as being fused at its N-terminus or C-terminus to a fusion partner.

The papillomavirus L2 fusion product may be characterized as having a fusion partner inserted between L2 amino acids.

The papillomavirus L1 product may be characterized as being a human papillomavirus L1 product or a bovine papillomavirus L1 product.

The human papillomavirus L1 product may be characterized as being a HPV16 L1 product and the bovine papillomavirus L1 product may be characterized as being a BPV1 L1 product.

The papillomavirus-like particle may consist essentially of HPV16L1 and HPV16L2-HPV16E7 (full-length), where HPV16E7 is fused to the C-terminus of HPV16L2, BPVL1 and BPVL2-HPV16E7 (full-length), where HPV16E7 is fused to the C-terminus of BPVL2, or BPVL1 and BPVL2-HPV16E7 (amino acids 1–30), where HPV16E7 is fused to BPVL2 between L2 amino acids 274 and 275.

According to another aspect of the invention, there is provided one or more synthetic DNA molecule or molecules characterized as singly or doubly encoding a papillomavirus L1 product and a papillomavirus L2 fusion product where the molecule or molecules direct expression in a transformed host cell of a papillomavirus-like particle, characterized as having conformational epitopes, comprising the papillomavirus L1 product and the papillomavirus L2 fusion product.

The transformed host cell may be an insect host cell (such as Sf9 insect host cell) and the DNA molecule or molecules may further comprise an insect cell vector (such as a baculovirus vector), or the transformed host cell may be a mammalian host cell and the DNA molecule or molecules may further comprise a mammalian cell vector (such as a vaccinia virus vector), or the transformed host cell may be a yeast host cell and the DNA molecule or molecules may further comprise a yeast cell vector.

According to another aspect of the invention, there is provided a host cell transformed with the DNA molecule or molecules of above.

According to yet another aspect of the invention, there is provided a method for using the DNA molecule or molecules of above comprising the steps of: providing conditions for the molecule or molecules of above to direct the above expression; and recovering the papillomavirus-like particle from the above transformed host cell.

According to still another aspect of the invention, there is provided a method for producing a papillomavirus-like particle, characterized as having conformational epitopes, comprising a papillomavirus L1 product and a papillomavirus L2 fusion product, which method comprises the step of providing conditions for the DNA molecule or molecules of above to direct the above expression in the above transformed host cell of the papillomavirus-like particle.

The invention also provides a method of purification of the papillomavirus-like particle of above comprising the step of exposing the papillomavirus-like particle to an affinity chromatography column, comprising antibodies that bind to a fusion partner of the papillomavirus L2 fusion product of the papillomavirus-like particle, resulting in the purification of the particle.

The invention further provides a method of purification of a fusion partner of the papillomavirus L2 fusion product of the papillomavirus-like particle of above comprising the step of isolating the papillomavirus-like particle of above resulting in the purification of the fusion partner.

The invention additionally provides a method of delivery into a cell of a fusion partner of the papillomavirus L2 fusion product of the papillomavirus-like particle of above comprising the step of administering the papillomavirus-like particle of above to the cell resulting in the delivery into the cell of the fusion partner.

The invention moreover provides a vaccine comprising the papillomavirus-like particle of above.

DETAILED DESCRIPTION OF THE INVENTION

This invention arises from the result that a papillomavirus L2 fusion product can become incorporated into a papillomavirus L1 product-based papillomavirus-like particle that presents conformational epitopes.

This result was unexpected.

In the papillomavirus study by Kirnbauer et al., J Virol 67:6929 (1993), supra, it was demonstrated that a single nonconserved amino acid change in L1 is responsible for efficient self-assembly of L1 into VLPs and the presentation of conformational epitopes, which seem to be required for induction and detection of clinically relevant immune reactivity. Thus, it could not be predicted whether a papillomavirus L2 containing a foreign peptide or protein could co-assemble with papillomavirus L1 into particles, given that a single amino acid substitution in L1 can abolish efficient self-assembly. Neither could it be predicted whether any resulting chimeric particles would retain the ability to induce or detect neutralizing antibodies or other immune related responses, given that a single amino acid substitution in L1 can bar the presentation of conformational epitopes.

A papillomavirus L2 fusion product is meant to include a chain of amino acids in which part of the chain comes from a L2 protein sequence and part of the chain comes from another protein sequence (or other protein sequences).

L2 fusion products are produced by splicing (in frame) an open reading frame for one protein (or a number of proteins) next to or into an open reading frame for L2.

Protein engineering is used to determine the structure of the L2 fusion product. In a routine exercise for protein engineers, they generate variants of the natural protein L2. The changes they make can be educated guesses based on detailed knowledge of the structure of L2; alternatively, changes can be made on a purely random basis. Or a combination of structural information with random mutagenesis and selection can have dramatic results.

For example, the selection of L2 amino acids between which to insert a fusion peptide or protein can be made on this basis. The existence of a region where amino acid sequence and length vary between papillomaviruses suggests that this region represents a structure that is nonessential for the integrity of L2 and/or its incorporation into particles. The observed ability to insert a fusion peptide or protein within L2 implies that such a region exists.

Determination of a structure for the L2 fusion product is performed on the basis of the ability of the L2 fusion product to become incorporated into a papillomavirus L1 product-based papillomavirus-like particle that presents conformational epitopes.

Preferred means of determining a structure include assays that measure the efficiency and/or authenticity of incorporation of an L2 fusion product into a papillomavirus L1 product-based papillomavirus-like particle.

The efficiency and/or authenticity of formation of L1/L2 VLPs is related to the presentation of conformational epitopes (supra).

The chimeric L2 will thus become incorporated into L1-based VLPs with an efficiency and/or authenticity similar to that of incorporation of wild-type L2.

Other preferred means of determining a structure for the L2 fusion product include assays that measure the induction and/or detection of neutralizing antibodies.

The induction and/or detection of neutralizing antibodies is related to the presentation of conformational epitopes, because neutralizing antibodies are directed against conformationally dependent epitopes (supra).

The incorporation of the chimeric L2 will thus not inhibit the induction and/or detection of neutralizing antibodies by chimeric papillomavirus-like particles as compared to L1 or L1/L2 VLPs.

For purposes of the invention, a chimeric L2 fusion product is capable of becoming incorporated into a papillomavirus L1 product-based papillomavirus-like particle that presents conformational epitopes, whether identified by the above means or any other means known in the art.

The structure of L2 and its fusion partner (and L1) is meant to include a full-length L2 protein (and L1 protein) and a full-length fusion partner protein, and their peptide fragments, whether N-terminus fragments, C-terminus fragments, or internal fragments, having at least about 20 amino acid residues, advantageously at least about 10 amino acid residues, and preferably at least about 5 amino acid residues. Type, subgroup and strain variations of L2 (and L1), and human allelic and species variations of the fusion partner protein, are expressly contemplated as falling within the scope of the invention. The invention also includes conservative variants of the full-length L2 protein (and L1 protein) and the full-length fusion partner protein, and their peptide fragments, where conservative amino acids are substituted for amino acid residues of wild-type L2 (and L1) and the fusion partner protein. To account for degeneracy of the genetic code, the invention also includes DNA coding for the same amino acid residues as does the DNA of the L2 (and L1) and fusion partner gene.

The chimeric papillomavirus-like particle itself is envisioned as incorporating any L2 fusion product with any L1 product from any papillomavirus, whether the genomes are closely related, or are distantly related, so long as incorporation into particles occurs. Thus, a L2 fusion product, for example, related to any of BPV-1, BPV-2, BPV-4, CRPV, DPV, EEPV, HPV-1, HPV-5, HPV-6, HPV-8, HPV-11, HPV-16, HPV-18, HPV-31 or HPV-33, can be incorporated into particles with any L1 product, for example, from any of the above virus, or any type, subgroup or strain variation of papillomavirus.

Because VLPs present conformationally dependent epitopes required for the induction of high titer neutralizing serum antibodies, VLP chimeras containing L2 fusion products can operate prophylactically as optimized subunit vaccines for the stimulation of humoral immunity to prevent papillomavirus infection and thereby preclude the development of papillomavirus associated cancers and other papillomavirus associated pathologies.

Because it is unlikely VLPs will prove effective as therapeutic vaccines to induce regression of existing papillomavirus proliferative lesions, as discussed above, chimeric VLPs can function to address this long-felt and heretofore unsatisfied need to develop a therapeutic vaccine.

Chimeric VLPs are expected to bind specific cell surface receptors, get internalized and be released into the cytoplasm, and thus be more likely to promote the presentation of peptides in conjunction with class I MHC molecules for display to cytotoxic T cells for the generation of cell-mediated immunity. This is in contrast to uncomplexed proteins that would not be expected to specifically enter cells, or to promote the presentation of peptides in the context of Class I MHC molecules to elicit a cytotoxic T cell response (being more likely, if at all, to promote the presentation of peptides to be linked to Class II MHC molecules and displayed to helper T cells).

Inclusion of one or more fusion partners as L2 fusion products would clearly be a cost effective way to generate an effective papillomavirus vaccine with a broad spectrum of utility, including therapy and improved prevention of clinical lesions.

The fusion partner may be selected from the list consisting of those fusion partners that would provide a method for expanding the potential targets of a VLP-based vaccine, for example, E6 or E7 peptide or full-length E6 or E7, other papillomavirus peptides or proteins, or peptides or proteins of other STD or infectious agents, e.g., Herpes simplex, HIV, *Chlamydia trachomatis, Neisseria gonorrhoeae*, and *Treponema pallidum*.

The L2 fusion product is not limited to a single fusion partner per L2 molecule, and may include additional fusion partners, for example, additional peptides or full-length proteins or combinations thereof derived from the same or different proteins linked in tandem. Also, more than one L2 fusion product may be co-assembled into a single VLP. For example, a L2 fusion product or chimeric VLP containing a viral target epitope may also be engineered to contain a binding domain of a co-stimulatory protein or an accessory receptor or ligand involved in immune reactivity, e.g., B7 (which interacts with CD28 on T cells), an intercellular adhesion molecule (ICAM), a lymphocyte functional antigen (LFA), a vascular cell adhesion molecule (VCAM-1), and a heat stable antigen (HSA). (To target the co-stimulators or ligands to the surface of VLPs, see Example 14.)

It will be appreciated that the actual preferred amounts of chimeric papillomavirus-like particles as vaccines in the prevention and/or treatment of disease will vary according to the specific compositions formulated, the mode of application, the particular situs and the organism being treated. Dosages for a given host can be determined using conventional considerations, e.g., by means of an appropriate, conventional vaccination protocol.

Alternatively, chimeric VLPs can used in a method of purification of VLPS. VLPs are useful per se as prophylactic vaccines and in immunodiagnostics (supra). Briefly, antibodies to the fusion partner are generated using standard immunological techniques, an affinity chromatography column is constructed using the antibodies, and the VLPs are subsequently purified in an affinity chromatography step.

Or, chimeric VLPs can be used in a method of purification of a fusion partner. For example, VLPs containing a L2-E7 fusion product may be useful as a means of obtaining correctly folded E7. It has been reported that a greater percentage of cervical cancer patients are seropositive for conformationally correct E7 than for denatured E7, as isolated from bacteria (Viscidi et al., Int. J. Cancer 55:780 (1993)). The in vitro transcription-translation system used to generate E7 in this report is laborious and expensive, and uses radio-labeled E7. It would be advantageous to purify chimeric E7 VLPs and use the material in an E7 ELISA. To avoid complications of seroreactivity with human L1 or L2, BPV-based particles could be used. Monitoring E7 seroreactivity, which correlates with cancer as opposed to premalignant disease, has been proposed to be useful to follow the course of disease in cervical cancer patients and to screen for reoccurrences (id.).

Optionally, chimeric VLPs can be used in a method of delivery of an intact and active protein into cells. This protein may be, for example, an enzyme, or a toxin or a drug. The chimeric VLPs are administered to the cells, either in vitro, in vivo, in situ, or ex vivo, and the protein is subsequently delivered into the cell where it functions for its intended purpose, for example, as an enzyme, or a toxin or a drug.

We have succeeded at generating chimeric papillomavirus-like particles incorporating E7 protein or peptide fused to L2.

A papillomavirus E7 gene when fused in frame to the 3' end of the L2 gene or within part of the L2 open reading frame expressed an L2-E7 fusion protein that, in the presence of L1 protein, was incorporated into virus-like particles. Efficiency and authenticity of incorporation of L2-E7 into VLPs was similar to that of the wild-type L2 protein. BPV L1/L2-E7 virus-like particles were found to induce neutralizing antibodies as effectively as BPV L1/L2 particles. Chimeric particles were observed to elicit humoral immunity specific for fusion partner epitopes in that rabbits immunized with L2-E7 chimeric particles generated antibodies directed against E7.

Having succeeded at generating chimeric papillomavirus-like particles opens the door to fusing virtually any protein or peptide to an L2 product for incorporation into chimeric papillomavirus-like particles.

We accomplished the production of chimeric VLPs by generating L2-E7 fusion proteins and expressing these proteins along with L1 via recombinant baculoviruses in insect cells. We generated three chimeric VLPs: HPV16L1 +HPV16L2-HPV16E7 (full-length), BPVL1+BPVL2-HPV16E7 (full-length) and BPVL1+BPVL2-HPV16E7 (aa 1–30).

BPV L2 was fused at its C-terminus end to HPV16 E7. HPV16 L2 was fused at its C-terminus end to HPV16 E7. Additionally, the first 30 codons of HPV16 E7 were inserted between codons 274 and 275 of BPV L2.

Sucrose gradient co-sedimentation and co-immunoprecipitation of L1 and the L2-E7 chimeras demonstrated the incorporation of the chimeric protein into the VLPs.

Transmission electron microscopy revealed that particles containing the L2-E7 fusion protein assembled with the same efficiency as L1 or L1/L2 VLPS, and were morphologically indistinguishable.

In vitro BPV1 neutralization assays demonstrated that the BPV L1-containing chimeric VLPs were capable of inducing neutralizing antisera. Titers were comparable to those obtained using BPV L1/L2 VLPs. Equivalent neutralizing titers of 30,000 were obtained for both BPVL1/L2 VLPs and BPVL1/L2-HPV16E7 (full-length) chimeric VLPs.

Rabbits immunized with L2-E7 chimeric particles generated antibodies directed against E7, demonstrating the induction by chimeric VLPs of humoral immunity specific for fusion partner epitopes, and also establishing the location of E7 epitopes as external to VLPs.

As set forth in Example 1, chimeric recombinant baculoviruses can be generated. Genes for the chimeras may be obtained from genomic sources or cDNAs, by direct synthesis, or by any combination thereof. L2 and its fusion partner genes can be amplified by recombinant PCR techniques, for example, with oligos containing restriction enzyme sites and complementarities that facilitate fusion and cloning into expression, transfer and/or cloning vectors, e.g., plasmids.

Fused genes can be cloned into a baculovirus expression vector. Another baculovirus expression vector containing L1can be generated. Or the fused genes can be cloned into a baculovirus double expression vector that already contains L1.

Example 2 sets forth a typical procedure for selection of recombinant baculoviruses. CsCl-purified (or equivalent) recombinant plasmid can be cotransfected with baculovirus DNA into Sf9 insect cells by using Lipofectin (or equivalent). The recombinant baculoviruses can then be plaque-purified (for example) using conventional baculovirus vector and insect cell culture procedures.

It may be advantageous to use two single expression baculovirus vectors instead of a double expression baculovirus vector. In this case, chimeric VLPs can be produced by infecting Sf9 cells with two recombinant baculoviruses, one encoding a L1 product and the other encoding the L2 fusion product. Locating the genes on different vectors facilitates manipulation of the amount of L1 product and L2 fusion product produced. This approach permits one to change the ratio of L2 fusion product to L1 product in a VLP. Although in native virions, L2 is the minor component as compared to L1, we can achieve greater incorporation of L2 fusion product into VLPs using two single expression vectors.

As set forth in Example 3, chimeric particles can be purified by banding in cesium chloride (or equivalent). Sf9 insect cells can be infected, for example, at a multiplicity of infection of 10 with recombinant baculoviruses. After 72 hours (or so), cells can be harvested and sonicated in a phosphate-buffered saline (or equivalent) for 60 sec (or so). After low speed clarification (or equivalent), the lysates can be subjected to centrifugation, for example, at 110,000×g for 2.5 h through a 40% (wt/vol) sucrose/PBS cushion (SW-28 rotor). The resuspended pellets can be centrifuged to equilibrium, for example, at 141,000×g for 20 h at room temperature in a 10–40% (wt/wt) CsCl/PBS gradient. The visible band can be harvested, centrifuged to equilibrium again by using the identical conditions, dialyzed extensively against PBS, and stored at 4° C. (for example).

As set forth in Example 4, co-sedimentation of chimeric complexes can be established, for example, by analytical gradient centrifugation. E.g., a 12 to 45% sucrose step gradient can be allowed to linearize overnight at 4° C., dialyzed samples can be layered on top, and the gradient can be centrifuged at 41,000 rpm (288,000×g) for 2 h in a SW-41 rotor. Fractions can be harvested and analyzed for co-sedimentation, for example, by Western blotting or co-immunoprecipitation.

As set forth in Example 5, co-sedimentation can be established, for example, by co-immunoprecipitation.

As set forth in Example 6, antisera can be produced. This can be done to conduct a BPV1 neutralization assay (or equivalent) as is described in Dvoretsky et al., Virology 103:369 (1980). E.g., antisera can be produced as follows. Rabbits can be immunized by subcutaneous injection of 330 μl of CsCl gradient-purified particles in PBS at a concentration of 1 mg/ml. Rabbits can then be boosted with the same amount of particles two weeks and four weeks after the primary injection.

As set forth in Example 7, a BPV1 neutralization assay (or equivalent) can be performed to test whether BPV chimeric particles present conformational epitopes. E.g., serial dilutions of sera obtained 3 weeks after the second booster injection can be incubated with ≈500 focus-forming units of BPV1 virus for 30 min, the virus can be adsorbed to C127 cells for 1 h, and the cells can be cultured for 3 weeks. Foci can then be stained with 0.5% methylene blue/0.25% carbol fuchsin in methanol. Neutralizing titers can be obtained for chimeric VLPs and control BPVL1-L2 VLPs. Equivalent neutralizing titers will indicate proper folding of the chimeric particles effective to present conformational epitopes.

As set forth in Example 8, chimeric particles can be assayed, for example, by transmission electron microscopy. E.g., purified particles can be adsorbed to carbon-coated grids, stained with 1% uranyl acetate, and examined with a Philips electron microscope model EM 400T at ×36,000 magnification. Efficiency of incorporation and morphology of chimeric particles and L1 or L1/L2 VLPs can be compared and contrasted. Indistinguishable efficiency of incorporation and morphology will indicate proper self-assembly of the chimeric particles.

As set forth in Example 9, chimeric particles can be assayed, for example, for induction of humoral immunity specific for fusion partner epitopes. E.g., rabbits can be inoculated with chimeric VLPs. The sera can be analyzed for antibodies, for example, by subjecting a sample of the fusion partner antigen to SDS-PAGE and then Western blotting. Immune and preimmune (control) sera can be applied at an appropriate dilution. Detection of the fusion partner band in the Western blot by serum from the immune rabbit indicates the induction of antibodies specific for fusion partner epitopes.

As set forth in Example 10, chimeric particles can be assayed, for example, for induction of cell-mediated immunity specific for fusion peptides, for instance, by injecting chimeric VLPs into mice, and measuring antigen-specific T cell proliferation.

As set forth in Example 11, chimeric particles can be assayed, for example, for induction of prophylactic immunity against challenge infection, for instance, by immunizing rabbits with chimeric CRPV VLPs and nonchimeric CRPV VLPs (control), and subsequently challenging with infectious CRPV, to demonstrate that L2 fusions do not abrogate prophylactic immunity; or by immunizing experimental animals with chimeric VLPs containing an STD agent, subsequently challenging with the STD agent, and measuring increased survival against lethal challenge or decreased infection following sub-lethal challenge.

As set forth in Example 12, chimeric particles can be assayed, for example, for induction of therapeutic immunity against pre-existing papillomas, for instance, by immunizing rabbits (that have pre-existing papillomas) using chimeric CRPV VLPs and nonchimeric CRPV VLPs (control), and measuring regression of the pre-existing papillomas.

As set forth in Example 13, chimeric particles can be assayed, for example, for immunotherapy and immunoprevention of tumors.

Particular aspects of the invention may be more readily understood by reference to the following examples, which are intended to exemplify the invention, without limiting its scope to the particular exemplified embodiments.

EXAMPLE 1

Generation of Chimeric Recombinant Baculoviruses

Three chimeras were generated: HPV16L2-HPV16E7, BPVL2-HPV16E7, and BPVL2-HPV16E7 (aa 1–30). HPV16L2-HPV16E7 contained the full-length HPV16E7 fused to the C-terminus (aa 473) of HPV16L2. BPVL2-HPV16E7 contained the full-length HPV16E7 fused to the C-terminus of BPVL2 (aa 469). BPVL2-HPV16E7 (aa 1–30) contained the first 30 amino acids of HPV16E7 fused to the middle of BPVL2 between amino acids 274 and 275.

L2-E7 chimeric genes were generated via recombinant PCR techniques (Higuchi, R. (1990) in PCR Protocols; A Guide to Methods and Applications, ed. Innis, M A, Gelfand, D H, Sninsky, J J, and White, T J. (Academic, New York), pp. 177–180). For the chimeras containing full-length HPV16E7, L2 was amplified with a 5' oligo containing a restriction enzyme site, and a 3' oligo which was complementary to the E7 5' oligo. In an independent reaction, E7 was amplified with a 5' oligo complementary to the L2 3' oligo and a 3' oligo containing a restriction enzyme site. The L2 and E7 genes were then fused in a second primer extension reaction using only the outside (L2 5', and E7 3') oligos. For the chimera containing only amino acids 1–30 of HPV16E7, the "internal" primers encoded the first 30 aa of HPV16E7.

The fused genes were then cloned into the baculovirus double expression vector pSynwtVI-, (which already contained L1 cloned under the polyhedrin promoter (Kirnbauer et al., Virol. 67:6929 (1993)) immediately downstream of the pSyn promoter.

The BPVL2-HPV16E7 chimeras were cloned as 5' BglII to 3' BglII fragments. The HPV16L2-HPV16E7 chimera was cloned as a 5' SstII to 3' SstII fragment. The primers used for BPVL2-HPV16E7 (full-length) were: BPVL2 sense,

5'GCGGTAGATCTACCTATAAATATGAGTGCACGAAAAAGAGTAAAACGT3' (SEQ ID NO:1), and antisense, 5'GCAATGTAGGTGTATCTCCATGCATGGCATGTTTCCGTTTTTTTCGTTTCCTCAACA AGGAGGG3' (SEQ ID NO:2), HPV16E7, sense, 5'CCCTCCTTGTTGAGGAAACGAAAAAAACGGAAACATGCCATGCATGGAGATACACCT ACATTGC3' (SEQ ID NO:3), and antisense,

5'CCGCTAGATCTGGTACCTGCAGGATCAGCCATGG3' (SEQ ID NO:4).

The primers used for BPVL2-HPV16E7 (aa 1–30) were as follows:

BPVL2, sense: same as above.
Internal primer, antisense,

5'CAGTTGTCTCTGGTTGCAAATCTAACATATATTCATGCAATGTAGGTGTATCTCCAT GCATGGATGAAAACACTTCAGGATCTTCCGTGGGC3' (SEQ ID NO:5).

Internal primer, sense,

5'GCATGAATATATGTTAGATTTGCAACCAGAGACAACTGATCTCTACTGTTATGAGCA ATTAAATGACCAAACATTTGCAAACCCACTGTATGAAGCAGAACC3' (SEQ ID NO:6).

BPVL2, antisense,

5'CCGCTAGATCTAGGGAGATACAGCTTCTGGCCTTGTTGCCACAACGC3' (SEQ ID NO:7).

The primers used for HPV16L2-HPV16E7 chimeras were as follows: HPV16L2, sense,

5'GCGGT<u>CCGCGG</u>AATATGCGACACAAACGTTCTGCAAAACGCACAAAACGT3' (SEQ ID NO:8), and antisense,

5'ATCTCCATGCATGGCAGCCAAAGAGAC3' (SEQ ID NO:9),

HPV16E7, sense,

5'GTCTCTTTGGCTGCCATGCATGGAGAT3' (SEQ ID NO:10), and antisense,

5'GCT<u>CCGCGG</u>GGTACCTGCAGGATCAGCC3' (SEQ ID NO:11).

EXAMPLE 2

Selection of Recombinant Baculoviruses

CsCl-purified recombinant plasmid was cotransfected with baculovirus DNA (Baculo-Gold; PharMingen, San Diego, Calif.) into Sf9 insect cells (ATCC, CRL 1711) by using Lipofectin (GIBCO/BRL, Gaithersburg, Md.) (Hartig, P. C. Biotechniques 11:310 (1991)). The recombinant baculoviruses were plaque-purified as described (Summers, M. D. & Smith, G. E. (1987) A Manual of Methods for Baculovirus Vectors and Insect Cell Culture Procedures, Texas Agricultural Experiment Station Bulletin (Tex. Agric. Exp. Stn., College Station, Tex.), Vol 1555).

EXAMPLE 3

Purification of Chimeric Particles

Sf9 insect cells were infected at a multiplicity of infection of 10 with recombinant baculoviruses. After 72 h, the harvested cells were sonicated in phosphate-buffered saline (PBS) for 60 sec. After low-speed clarification, the lysates were subjected to centrifugation at 110,000×g for 2.5 h through a 40% (wt/vol) sucrose/PBS cushion (SW-28 rotor). The resuspended pellets were centrifuged to equilibrium at 141,000×g for 20 h at room temperature in a 10–40% (wt/wt) CsCl/PBS gradient. The visible band was harvested, centrifuged to equilibrium again by using the identical conditions, dialyzed extensively against PBS, and stored at 4° C.

EXAMPLE 4

Co-Sedimentation of L1/L2-E7 Complexes

To determine whether the L2-E7 fusion protein was incorporated into particles, analytical gradient centrifugation was performed as previously described for determining the co-assembly of L1 and L2 (Kirnbauer et al., Virol. 67:6929 (1993)).

Briefly, a 12 to 45% sucrose step gradient was allowed to linearize overnight at 4° C., dialyzed samples were layered on top, and the gradient was centrifuged at 41,000 rpm (288,000×g) for 2 h in a SW-41 rotor. Fractions were harvested. The fractions were analyzed by Coomassie stained SDS-PAGE (L1) or Western blotting with an anti-BPVL2 polyclonal Ab, or anti-HPV16E7 polyclonal Ab, and $^{125}$I-labeled anti-rabbit IgG.

Association of the chimeric L2-E7 with the virus-like particles was established by co-sedimentation.

EXAMPLE 5

Co-Immunoprecipitation of L1/L2-E7 Complexes

To obtain evidence that the L2-E7 fusion proteins formed stable complexes with L1, co-immunoprecipitation experiments were performed.

Briefly, BPVL1/L2-HPV16E7 (full-length) and BPVL1/L2-HPV16E7 (aa 1–30) VLP preparations were immunoprecipitated in PBS, 1% Triton® X-100 with anti-L1 Mab 5B6 (Roden et al., J. Virol., in press, (November, 1994)), an anti-L1 polyclonal Ab, pre-immune serum or an irrelevant Ab (anti-E1A Mab) and protein A-Sepharose and subjected to SDS-PAGE. Proteins were immunoblotted and probed with anti-BPVL2, or anti-HPV16E7 sera, or an anti-HPV16E7 Mab (Triton Diagnostics, Alameda, Calif.).

Association of the chimeric L2-E7 with the virus-like particles was established by co-immunoprecipitation.

EXAMPLE 6

Production of Antisera

Rabbits were immunized by subcutaneous injection of 330 ul of CsCl gradient-purified particles in PBS at a concentration of 1 mg/ml. Rabbits were boosted with the same amount of particles two weeks and four weeks after the primary injection.

EXAMPLE 7

BPV1 Neutralization Assay

A focus-forming assay was performed as described (Kirnbauer et al., Proc. Natl. Acad. Sci. USA 89:12180 (1992)).

Briefly, serial dilutions of rabbit sera obtained 3 weeks after the second booster injection were incubated with ≈500 focus-forming units of BPV1 virus for 30 min, the virus was adsorbed to C127 cells for 1 h, and the cells were cultured for 3 weeks (Dvoretzky et al., Virology 103:369 (1980)). The foci were stained with 0.5% methylene blue/0.25% carbol fuchsin in methanol.

Equivalent neutralizing titers of 30,000 were obtained for the BPVL1/L2 VLPs and BPVL1/L2-HPV16E7 (full-length) chimeric VLPs.

EXAMPLE 8

Electron Microscopy

Transmission electron microscopy was performed as described (Kirnbauer et al., Proc. Natl. Acad. Sci. USA 89:12180 (1992)).

Briefly, purified particles were adsorbed to carbon-coated grids, stained with 1% uranyl acetate, and examined with a Philips electron microscope model EM 400T at ×36,000 magnification.

Particles containing the L2-E7 fusion protein were found to be indistinguishable from L1 or L1/L2 VLPs in terms of morphology and efficiency of incorporation.

EXAMPLE 9

Induction of Antibodies

Rabbits inoculated with BPVL1/L2-HPV16E7 papillomavirus-like particles produced antisera that recognized E7.

To analyze the sera for E7 specificity, 2.5 μg of HPV16E7 and 2.5 μg of BSA (control) were subjected to SDS-PAGE and then Western blotted. Immune and preimmune (control) sera were applied at a dilution of 1:10.

Serum from the immune rabbit specifically detected the HPV16E7 protein band in the Western blot, indicating the induction of antibodies specific for E7 epitopes.

EXAMPLE 10

Induction of Cell-Mediated Immunity

Chimeric particles are assayed for induction of cell-mediated immunity specific for E7 peptides, for example, by injecting chimeric VLPs into mice, and measuring antigen-specific T cell proliferation.

EXAMPLE 11

Prophylactic Immunity

Chimeric particles are assayed for induction of prophylactic immunity against challenge infection, for example, by immunizing rabbits with E7 chimeric CRPV VLPs and nonchimeric CRPV VLPs (control), and subsequently challenging with infectious CRPV, to demonstrate that L2-E7 fusions do not abrogate prophylactic immunity; or by immunizing experimental animals with chimeric VLPs containing an STD agent, subsequently challenging with the STD agent, and measuring increased survival against lethal challenge or decreased infection following sub-lethal challenge.

EXAMPLE 12

Therapeutic Immunity

Chimeric particles are assayed for induction of therapeutic immunity against pre-existing papillomas, for example, by immunizing rabbits (that have pre-existing papillomas) using E7 chimeric CRPV VLPs and nonchimeric CRPV VLPs (control), and measuring regression of the pre-existing papillomas.

EXAMPLE 13

Immunotherapy and Immunoprevention of Tumors

Chimeric particles are assayed for the ability to prevent tumor development or to treat existing tumors, for example, in experimental animals such as mice using tumor cells expressing, e.g., E7. Animals are immunized with, e.g., L2-E7 chimeric VLPs and tested for growth of inoculated tumorigenic cells that express, e.g., E7. This approach has been shown to work for animals immunized with noncomplexed E7 and a co-stimulatory protein (Chen et al., Proc. Natl. Acad. Sci. USA 88:110 (1991)).

EXAMPLE 14

Targeting the Surface of Chimeric VLPs

It may be desirable for certain molecules, such as co-stimulators or ligands that bind to cell-surfaces, to be present on the surface of chimeric VLPs. Roden et al., J. Virol., in press, (November, 1994) determined that regions of L2 are located on the surface of VLPs. A peptide composed of BPV L2 amino acids 44–173, when inoculated into rabbits, induced neutralizing antibodies that were active at a 1:1000 serum dilution. These results indicate that regions of L2 specify neutralizing epitopes, and that these regions are therefore accessible to the surface of native virions. Consequently, fusing a non-L2 polypeptide to one of these regions would likely result in the targeting of this polypeptide to the surface of a chimeric VLP.

While particular embodiments of the invention have been described in detail, it will be apparent to those skilled in the art that these embodiments are exemplary rather than limiting, and the true scope of the invention is that defined within the appended claims.

What is claimed is:

1. A papillomavirus-like particle having conformational epitopes comprising a papillomavirus L1 fusion product.

2. The papillomavirus-like particle of claim 1 wherein said papillomavirus L1 fusion product is a human papillomavirus L1 fusion product or a bovine papillomavirus L1 fusion product.

3. The papillomavirus-like particle of claim 2 wherein said human papillomavirus L1 fusion product is a HPV16 L1 fusion product and said bovine papillomavirus L1 fusion product is a BPV1 L1 fusion product.

4. The papillomavirus-like particle of claim 1 wherein said papillomavirus L1 fusion product comprises a fusion partner that is a peptide or a full-length protein, or comprises fusion partners that include peptides or full-length proteins or combinations thereof linked in tandem.

5. The papillomavirus-like particle of claim 4 wherein said fusion partner is a papillomavirus E6 or E7 product.

6. The papillomavirus-like particle of claim 1 wherein said papillomavirus L1 fusion product is fused at its N-terminus or C-terminus to a fusion partner.

7. The papillomavirus-like particle of claim 1 wherein said papillomavirus L1 fusion product has a fusion partner inserted between L1 amino acids.

8. The papillomavirus-like particle of claim 1 further comprising a papillomavirus L2 product.

9. The papillomavirus-like particle of claim 8 wherein said papillomavirus L2 product is a HPV16 L2 product or a BPV1 L2 product.

10. A composition comprising the papillomavirus-like particle of claim 1.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

GCGGTAGATC TACCTATAAA TATGAGTGCA CGAAAAAGAG TAAAACGT     48

( 2 ) INFORMATION FOR SEQ ID NO:2:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

GCAATGTAGG TGTATCTCCA TGCATGGCAT GTTTCCGTTT TTTTCGTTTC CTCAACAAGG     60

AGGG     64

( 2 ) INFORMATION FOR SEQ ID NO:3:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

CCCTCCTTGT TGAGGAAACG AAAAAAACGG AAACATGCCA TGCATGGAGA TACACCTACA     60

TTGC     64

( 2 ) INFORMATION FOR SEQ ID NO:4:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

CCGCTAGATC TGGTACCTGC AGGATCAGCC ATGG     34

( 2 ) INFORMATION FOR SEQ ID NO:5:

( i ) SEQUENCE CHARACTERISTICS:
   ( A ) LENGTH: 92 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

CAGTTGTCTC TGGTTGCAAA TCTAACATAT ATTCATGCAA TGTAGGTGTA TCTCCATGCA    60

TGGATGAAAA CACTTCAGGA TCTTCCGTGG GC    92

( 2 ) INFORMATION FOR SEQ ID NO:6:

( i ) SEQUENCE CHARACTERISTICS:
      ( A ) LENGTH: 102 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

GCATGAATAT ATGTTAGATT TGCAACCAGA GACAACTGAT CTCTACTGTT ATGAGCAATT    60

AAATGACCAA ACATTTGCAA ACCCACTGTA TGAAGCAGAA CC    102

( 2 ) INFORMATION FOR SEQ ID NO:7:

( i ) SEQUENCE CHARACTERISTICS:
      ( A ) LENGTH: 47 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:7:

CCGCTAGATC TAGGGAGATA CAGCTTCTGG CCTTGTTGCC ACAACGC    47

( 2 ) INFORMATION FOR SEQ ID NO:8:

( i ) SEQUENCE CHARACTERISTICS:
      ( A ) LENGTH: 50 base pairs
      ( B ) TYPE: nucleic acid
      ( C ) STRANDEDNESS: single
      ( D ) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:8:

GCGGTCCGCG GAATATGCGA CACAAACGTT CTGCAAAACG CACAAAACGT      50

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:9:

ATCTCCATGC ATGGCAGCCA AAGAGAC      27

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:10:

GTCTCTTTGG CTGCCATGCA TGGAGAT      27

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

( v i ) ORIGINAL SOURCE:

( x i ) SEQUENCE DESCRIPTION: SEQ ID NO:11:

GCTCCGCGGG GTACCTGCAG GATCAGCC 28